United States Patent [19]

Huffman

[11] 4,382,787
[45] May 10, 1983

[54] DENTAL MODEL ARTICULATOR

[75] Inventor: Ronald E. Huffman, Tucson, Ariz.

[73] Assignee: KV33 Corporation, Tucson, Ariz.

[21] Appl. No.: 261,562

[22] Filed: May 7, 1981

[51] Int. Cl.³ .............................................. A61C 11/00
[52] U.S. Cl. ....................................................... 433/64
[58] Field of Search ............................... 433/54, 57, 64

[56] References Cited

U.S. PATENT DOCUMENTS

| 824,096 | 6/1906 | Crate ...................................... | 433/55 |
| 3,429,045 | 2/1969 | Anderson et al. ..................... | 433/54 |
| 3,466,750 | 9/1969 | Timberlake et al. ................. | 433/54 |

FOREIGN PATENT DOCUMENTS 572850 11/1958 Belgium ................................ 433/64

Primary Examiner—Robert Peshock
Attorney, Agent, or Firm—Cahill, Sutton & Thomas

[57] ABSTRACT

A mounting for casts of a dental model correlates the casts with the condition to be redintegrated throughout a full range of occlusal and masticatory registration. The mounting includes separate duplicate members, each of which members is attachable to a cast of a dental model and supports a spherical cavity, and an hinged two part flexible element, each of which parts is a mirror image of the other and supports a sphere to be positioned within respective ones of the spherical cavities and adhesively secured thereto after alignment of the paired casts. Simulation and tracing the paths of natural occlusal and masticatory registration is effected by pivotal movement about the hinge line and flexing of the element.

30 Claims, 5 Drawing Figures

DENTAL MODEL ARTICULATOR

Correlators or articulators for use with casts of a dental model to develop prosthetic dentures or denture elements have been used for a number of years. These articulators range from a very simple device affording only fixed pivotal movement between a pair of casts to highly sophisticated and mechanically complex devices which are capable of simulating the full range of occlusal and masticatory registration unique to any patient. The relatively simple devices are generally inadequate to provide sufficiently accurately registered prosthetic restoration to avoid extensive visits with a dentist to obtain adjustments thereof while the very complex devices are time consuming to operate and require extensive training to use properly. In either situation, the costs incurred to the patient are substantial. Moreover, none of the prior art articulators permit disengagement of the casts from registration with one another without extensive realignment upon reengagement. Thus, a technician is usually forced to perform his work while the casts are mounted on the articulator. Such an environment is difficult to work in with speed and accuracy.

Each of the following listed United States patents are directed to dental articulators which incorporate lockable ball and socket elements to afford pivotal movement and extensible members to afford translational movement: Nos. 175,046, 530,524, 537,812, 565,326, 981,430, 1,736,006, 1,841,728, 2,571,280, 2,600,899, 2,608,762, 2,621,407, 2,765,533, 4,169,314 and 4,196,518.

An articulator which provides structure to effect a simple hinged movement without provision of mechanical structure for defining translatory movement or multi-axis pivotal movement is disclosed in U.S. Pat. No. 2,430,177. Simulation of the full range of occlusal and masticatory registration is obtained by resiliently flexing the articulator. Such resiliency is afforded by the coil spring like configuration of a wire element defining each leg of two pairs of legs. For a well trained and experienced technician, the freedom of movement afforded by this articulator is sufficient to permit the formation and adjustments of most prosthetic dentures. Accurate use of the device is predicated upon the formation within each cast of a dental model elongated sockets for receiving, capturing and retaining each of the four wire legs. The casts usually vary in overall physical size, depending upon the size of the patient's teeth to be simulated and the size and configuration of the base formed. To employ the articulator described in this patent, uniformity of spacing between the pairs of sockets in each pair of casts is of paramount importance. The demands imposed by such uniform spacing during formation of the casts is time consuming and requires an experienced technician. No adjustment capability exists within the articulator itself to accommodate differences in spacing, as would be expected as the size of pairs of casts vary in proportion to the physical size of the patient's jaws and the usually uniquely sized bases therefor.

The present invention is directed to an inexperience throw away articulator for dental models. The articulator includes a pair of members, each of which members is adhesively attachable to a cast of a pair of casts of a dental model. A semi-spherical cavity is disposed in each member. A two part hinged element or pair of brackets of flexible resilient material includes a centrally located snap fit hinge and a sphere disposed at the extremity of each bracket. One of these spheres is locatable in each of the semi-spherical cavities in a member. Temporary retention therein may be effected by means of a pair of prongs of fingers extending from the opposed sides of each spherical cavity. Upon alignment of the casts with one another, each sphere is adhesively attached within its respective socket and the casts become hingedly attached to one another. Simulation of the full range of natural occlusal and masticatory registration is effected by a combination of pivotal movement about the hinge line and flexing of the respective brackets. The snap fit hinge permits rapid disassembly and reassembly without the need of realignment to effect proper registration between the casts; accordingly, a technician can readily perform his work on the casts or dental restoration in comfort by placing the cast to be worked upon a work surface or in a holder.

A primary object of the present invention is to provide apparatus for operatively simulating the occlusal and masticatory relationships to be redintegrated.

Another object of the present invention is to provide apparatus for mounting and adjustably holding casts of a dental model to simulate their natural registration to facilitate precise occlusal and masticatory correlation of a dental restoration.

Still another object of the present invention is to provide apparatus for resiliently associating operatively interconnecting spaced dental model casts for relative adjustment thereof throughout the range of a full spherical orbit.

Yet another object of the present invention is to provide a manipulatable apparatus to check, trace, fit and polish a dental restoration upon a dental model against and for occlusal and masticatory registration.

A further object of the present invention is to provide an articulator for dental models which is simple and inexpensive to manufacture and operable throughout a wide range of relative adjustments.

A still further object of the present invention is to provide a throw-away articulator readily attachable to paired dental model casts within a wide range of alignment therebetween.

A yet further object of the present invention is to provide a four piece dental articulator, two pieces of which are duplicates and the remaining two pieces of which are mirror images of one another.

A yet further object of the present invention is to provide an articulator for supporting a pair of casts which articulator can be disassembled by disengaging snap fit pivots and assembled without need for realignment of the casts by engaging the snap fit pivots.

A yet further object of the present invention is to provide an articulator which is rapidly adaptable to support a pair of casts in registration.

A yet further object of the present invention is to provide an articulator which permits a technician to work on a cast physically independent of the other cast without affecting registration therebetween on reassembly of the articulator.

These and other objects of the present invention will become apparent to those skilled in the art as the description thereof proceeds.

The present invention may be described with greater specificity and clarity with reference to the following drawings, in which.

In the practice of prosthetic dentistry, one very important technical problem is the shaping and fitting of the restoration occlusal surfaces to register, meet and operatively cooperate with opposed surfaces in conformity with the established habits, idiosyncrasies and tooth facet inclinations of the user. The many factors peculiar to the individual have heretofore made proper operative correlation of the restoration with the associated dental elements almost invariably a matter susceptible of satisfactory resolution only through repetitious adjustments and modifications had in the dental chair after installation of the restoration. This occurs despite the use of fixed, even though adjustable, mechanically simulated axes of articulation, planes and arcs of occlusion, lines, planes and axes of symmetry and the like which fail to provide the full orbital range necessary for reconstitution of the natural dental relationships determinable from the traces and indices upon and established through use of the original dentures. To facilitate attainment of the desired operative registration between restorations and their associated dental elements and thereby largely obviate the necessity for adjustments and corrections in the dental chair, the present invention provides a device for laboratory use wherein the relationships to be redintegrated can be fully and accurately portrayed and operatively duplicated as a check mounting for the restoration.

The present invention is a device which hingedly, yieldably and separably associates for registration a pair of casts of a dental model in spaced opposition and which provides relative manipulation of the casts throughout a full spherical orbit wherein every phase and condition of dental occlusive attitude may be exemplified.

In practice, the casts of both the upper and lower natural dentures along with the conditions thereof requiring restoration or correction are made by well known techniques. The casts are secured to the present invention to register in simulation of the natural relationships they portray when in spaced substantially parallel relationship at one limit of the range of relative movement, which position is determinable by the structure of the invention. Through the novel features, structure and characteristics of the invention correlating the restoration or correction and the facet disposition and inclination thereof with the operative range and pattern of movement of the original dentures becomes possible.

Figure 1:
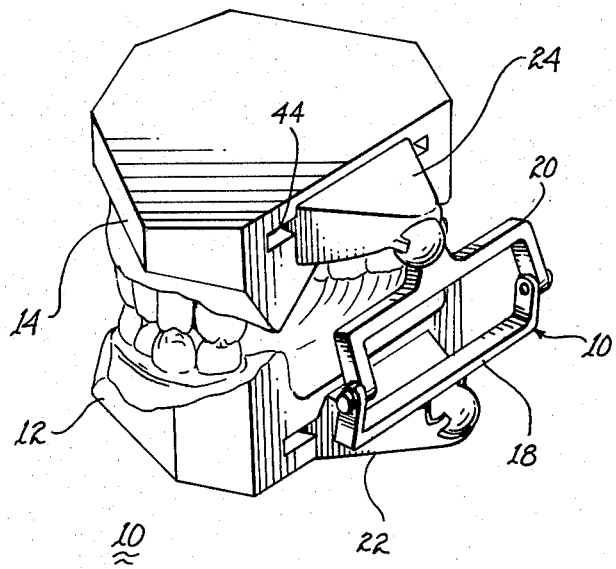
FIG. 1 is a perspective view illustrating the articulator supporting a pair of casts of a dental model.

Referring to FIG. 1, there is shown a complete dental model 10 having a pair of mating dental model casts 12 and 14 simulative of the original dentures and the condition requiring restoration or correction. An articulator 16 is attached to the casts to maintain them positionally simulative of the natural relationships portrayed when substantially in parallel relationship at one limit of the range of relative movement. A pair of interconnecting elements or brackets 18 and 20 are pivotally attached to one another and are of resilient flexible material sufficient to accommodate relative movement about all axis and within all planes between the casts in simulation of the operative range and pattern of the original dentures.

Referring jointly to the remaining figures, further details of articulator 16 will be described. First and second mounting means 22 and 24 are attached to casts 12 and 14, respectively. Each mounting means includes a semi-spherical or partially spherical depression disposed at the respective extremity. In example, mounting means 22 includes depression 26 and mounting means 24 includes depression 28. Brackets 18 and 20 each include a sphere (spheres 30, 32) sized to receivingly mate with depressions 26, 28. Brackets 18 and 20 are pivotally joined to one another by pivot means 34, 36; preferably, the pivot means is of the snap fit type.

To mount articulator 16, mounting means 22 and 24 are attached to the rear faces of the respective casts. Spheres 30 and 32 are located within their respective depressions 26, 30 upon angular adjustment of the respective brackets to obtain the requisite spatial relationship therebetween; nominally, the brackets define an interior obtuse angle. To maintain the casts in the predetermined fixed spatial relationship to one another at one limit of the range of relative movement, an adhesive is applied intermediate the spheres and their respective depressions to fixedly secure the respective bracket in fixed angular orientation with respect to the mounting means. Pivotal movement of the casts is effected by relative angular displacement between the joined brackets about the respective pivot means or hinge line. Translational movement in any plane and rotational movement about any axis of the casts with respect to one another is accommodated by the flexibility of brackets 16 and 18 (as shown in dashed lines in FIG. 4).

With the above general understanding of the basic function and structure of the invention, it may be beneficial to review and analyze certain nuances of the invention which render it of great practical benefit in the field of dental correction and restoration.

Figure 2B:
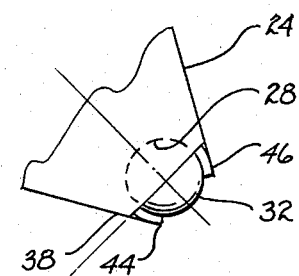
FIG. 2b is a partial top view of the articulator.

Mounting means 22 and 24 (See FIGS. 1, 2a, 2b, 4 and 5) may be generally triangular in one plane as illustrated in FIGS. 1 and 2b to provide an apex 38 within which depression 28 is formed. Base 40 (See FIG. 2a) of mounting means 24 may include a ridge or tab 42 for mechanical engagement with a slot 44 formed in the rear surface of the casts. The resulting mechanical engagement, in combination with mastic or adhesive disposed therebetween rigidly secures each mounting means to its respective cast.

During initial alignment and attachment of the brackets to the mounting means, maintenance of the casts in a predetermined relationship is critical. To simplify the manipulation during attachment, retaining fingers 44 and 46 extend from apex 38. These fingers are of resilient material and, in the quiescent state, cant toward one another to provide snap retention for a sphere 32 inserted within depression 38. Similar fingers extend from the apex of mounting means 22 to engage a sphere 30. With the use of such fingers, articulator 16 is retained in place during positioning of casts 12 and 14 and the need for manually retaining the articulator in place during such orientation of the casts is obviated. Upon achievement of the orientation of the casts, an adhesive, such as any one of the commercially available fast setting cyanoacrylate or anerobic adhesives, may be employed to secure each sphere within its respective depression.

Articulator 16 is formed of a pair of mirror image brackets, each of which includes a base 48 and a pair of arms 50, 52. The base supports a sphere, which sphere may be located slightly off center such that upon mating of the brackets, a line drawn through the center of the spheres is orthogonal to a line representative of the pivot axis of the articulator. Arms 50 and 52 may be formed to include complementary elements to establish the pivot means. In example, one arm may include a slot terminating in a circular bearing surface while the other arm may include a pin extending therefrom for retentative engagement with a corresponding slot and bearing surface. The pin, molded or otherwise formed upon fabrication of each of brackets 18 and 20, may be a simple shaft 54 extending therefrom and terminated by an end plate 56. The space intermediate the arm and end plate is generally equivalent to the width of the arm to be disposed therebetween into slotted retention with the shaft. Alternatively, each arm may include an aperture penetrably engageable by ancillary pin means or the like.

Preferably, the pivot means is of the snap fit type such that disengagement and reengagement of the brackets (and the supported casts) may be readily effected. Upon reengagement, the casts will be in registration with one another as no adjustments or parameters affecting registration are disturbed by disengagement/reengagement of the pivot means.

Figure 5:
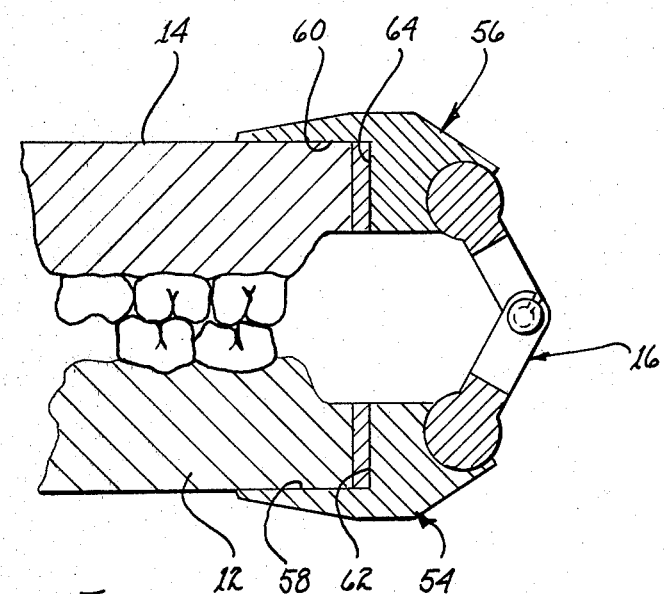
FIG. 5 is a partial cross-sectional view of the articulator and showing a variant of the dental model mounting means.

A variant of mounting means 22, 24, is illustrated in FIG. 5. Herein, mounting means 54 and 56 define right angled seats 58, 60, which seats may be juxtaposed with the rear and bottom faces of casts 12 and 14 to provide structural rigidity therebetween and a substantial surface area for adhesively securing the mounting means to the casts. To use the adhesive as a mechanical lock in addition to its adhering qualities, slots 62, 64 may be formed in one or both faces of seats 58, 60, respectively, to receive the mastic or adhesive employed and thereby provide a more strong bond. Each of mounting means 54 and 56 includes depressions as described above which may or may not include fingers for mechanically retaining the spheres to be mounted within the depressions.

Figure 2A:
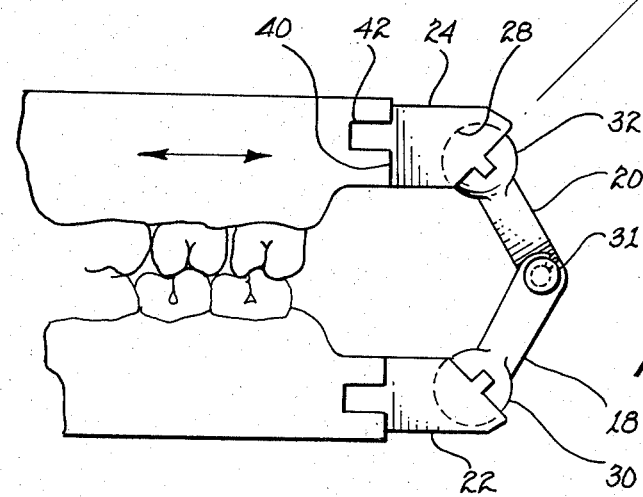
FIG. 2a is a partial cross-sectional view illustrating the elements of the articulator.
Figure 3:
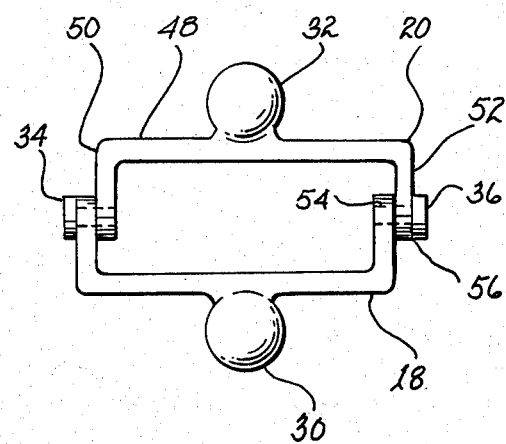
FIG. 3 illustrates the interconnecting element of the articulator.
Figure 4:
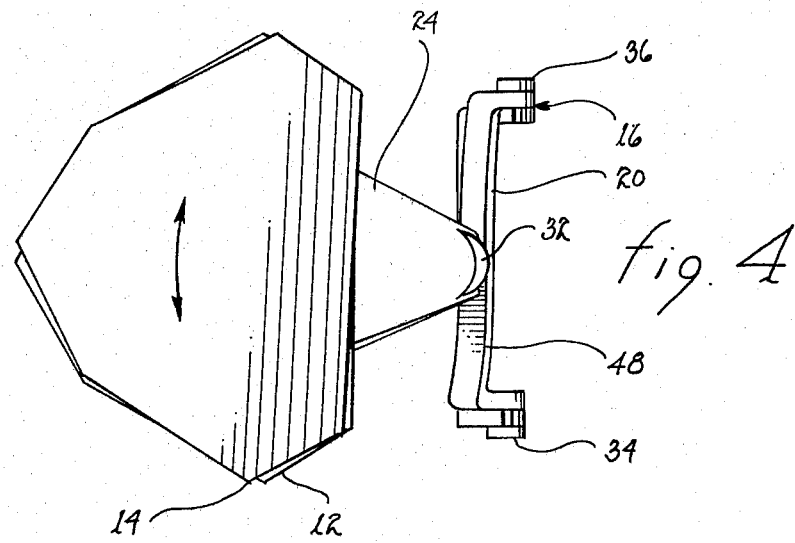
FIG. 4 is a partial top view of the articulator illustrating the flexibility of the interconnecting element.

In operation, the mounted casts may be relatively approached, separated, traversed, protruded, retracted, inclined and rotated through every possible condition and position of occlusal and masticatory registration, as shown by the arrows in FIGS. 1, 2a and 4, by simple manipulation to flex the brackets of the articulator. The resiliently yieldable brackets accommodate all deviation from the initial position of the casts to the extent necessary to fully manifest the operative variations of position inherent in the natural dentures.

After fabrication of a restoration and fitting of same to the appropriate cast, the casts may be manipulated to trace the normal occlusal registration of the dentures as determined by the facet inclinations of the natural teeth and the operative correlation of the restoration with the condition to be redintegrated may be checked for correction and precise fitting. The restoration may be removed from the respective cast with or without physical severance of the casts from one another. By severing the brackets from one another at the pivot means, the casts readily become physically separated from one another and work on the restoration may become more facile. On completion of the work, the casts are rejoined to one another by rejoining the brackets at the pivot means. The severance capability, without an accompanying obligation or requirement to realign or even check the alignment of the casts, is of immense importance to the dental technician's efficiency. After severance, each cast may be worked or physically independent of the other and positioned upon or retained by a work surface which surface can support the cast at an orientation most favorable for the type and nature of the work to be done. And, a check of the accuracy of the work can be made in a matter of seconds by simply snapping the elements of the pivot means together to engage the two brackets with one another and then simulate and trace the paths of natural and masticatory registration.

While the principles of the invention have now been made clear in an illustrative embodiment, there will be immediately obvious to those skilled in the art many modifications of structure, arrangement, proportions, elements, materials, and components, used in the practice of the invention which are particularly adapted for specific environments and operating requirements without departing from those principles.

I claim:

1. An articulator for correlating the casts of a dental model, said articulator comprising in combination:
   (a) a pair of mounting means, one of said mounting means being attachable to each cast;
   (b) a pair of resiliently flexible U-shaped mirror image brackets for operatively engaging said mounting means with one another to accommodate movement of the casts relative to one another, each said bracket including a pair of legs extending from a base and pivot means disposed at the extremity of each leg for pivotally engaging the corresponding leg of an interconnected bracket;
   (c) pivot means for pivotally interconncting the brackets of said pair of brackets to provide pivotal movement of the casts relative to one another about a pivotal axis, said pivot means including pin means disposed at the extremity of one leg and bearing surface means disposed at the extremity of an interconnected leg for pivotally engaging said pin means, said pin means including an end plate for defining a space intermediate said leg and said end plate to receive said interconnected leg supporting said bearing surface means and preclude lateral translation of said brackets relative to one another along the axis of rotation of said pin means, said bearing surface including a slot terminating in a circular bearing surface to provide a snap fit for said pin means;
   (d) a socket disposed in each of said mounting means and a ball attached to each of said brackets for engagement with the respective one of said sockets said socket including a pair of fingers for retaining said ball for attaching and fixedly retaining said pair of brackets to said pair of mounting means at any selectable angle within a range of predetermined angles in any of the axis of rotation to angularly orient one of the casts with respect to the other cast at any selectable angle within a range of angles about three axis of rotation and to locate one of the casts with respect to the other cast within two planes of translation.

2. The articulator as set forth in claim 1 wherein said brackets of each pair of brackets are mirror images of one another.

3. An articulator for correlating the casts of a dental model, said articulator comprising in combination:
   (a) a mounting attachable to each cast;
   (b) a pair of resiliently flexible brackets, each said bracket having a pair of legs;

(c) means for pivotally connecting one end of said pair of legs of each bracket to one another through pivoting snap fit joints pivotable about a common axis;

(d) means for interconnecting each said mounting with the other end of one bracket of said pair of brackets, said interconnecting means comprising a ball and socket joint wherein one of the ball and socket of said ball and socket joint is formed in said mounting and wherein the other of the ball and socket of said ball and socket joint extends from said bracket;

(e) means for fixing the angular relationship between each said mounting and the interconnected one of said pair of brackets after registration of the casts relative to one another by adjusting the angular relationship between each said mounting and its engaged one of said pair of brackets and by adjusting the angular relationship about the pivot axis between the pivotally connected ends of said pair of brackets; and (f) means for restraining separation between each said mounting and its engaged one of said pair of brackets during and after registration of the casts, said restraining means being independent of said fixing means.

4. The articulator as set forth in claim 3 wherein said restraining means comprises a resilient element formed as part of each said ball and socket joint for urging retention of the ball in its socket.

5. The articulator as set forth in claim 4 wherein said resilient element comprises a pair of fingers extending from the socket for gripping the ball.

6. The articulator as set forth in claim 5 wherein said fixing means comprises an adhesive disposed intermediate the ball and socket of each said ball and socket joint.

7. The articulator as set forth in claim 3 wherein said socket of said ball and socket joint is formed in said mounting and wherein said ball of said ball and socket joint extends from said bracket.

8. The articulator as set forth in claim 3 wherein said pair of brackets are configured as mirror images of one another.

9. The articulator as set forth in claim 3 wherein said connecting means attendant said brackets is formed as an integral part of said brackets.

10. The articulator as set forth in claim 3 wherein said interconnecting means includes two elements, one of said elements being formed as an integral part of said mounting and the other of said element being formed as an integral part of the engaged one of said brackets.

11. The articulator as set forth in claim 10 wherein said connecting means attendant said brackets is formed as an integral part of said brackets.

12. The articulator as set forth in claim 1 wherein said articulator consists of four parts comprising said pair of brackets and two of said mountings.

13. The articulator as set forth in claim 12 wherein said pair of brackets are configured as mirror images of one another.

14. The articulator as set forth in claim 3 wherein each of the casts includes a rear surface having a channel formed therein and wherein said mounting includes a tab for penetrably engaging the channel to aid in attaching said mounting to the cast.

15. The articulator as set forth in claim 3 wherein each of the casts includes two planar surfaces intersecting at the rear of the cast and wherein said mounting includes two planar intersecting surfaces juxtapositionable with the intersecting surfaces of the cast to aid in attaching said mounting to the cast.

16. The articulator as set forth in claim 12 wherein each of the casts includes a rear surface having a channel formed therein and wherein said mounting includes a tab for penetrably engaging the channel to aid in attaching said mounting to the cast.

17. The articulator as set forth in claim 12 wherein each of the casts includes two planar surfaces intersecting at the rear of the cast and wherein said mounting includes two planar intersecting surfaces juxtapositionable with the intersecting surfaces of the cast to aid in attaching said mounting to the cast.

18. A method for mounting casts of a dental model to afford correlation of the casts throughout a full range of occlusal and masticatory registration, said method comprising the steps of:

(a) attaching a mounting to each cast;

(b) pivotally connecting along a pivot axis one end of a first bracket with one end of a second bracket;

(c) interconnecting each mounting with the other end of one of the brackets through a pivot mechanism providing pivotal freedom between each mounting and its connected bracket about any axis of a set of intersecting orthogonal axis;

(d) positioning the casts relative to one another at one end of the range of occlusal and masticatory registration to be redintegrated by adjusting the angular relationship about any or all pivot axis between each mounting and its engaged bracket and by adjusting the angular relationship about the pivot axis between the pivotally connected ends of the brackets;

(e) immobilizing the angular relationship between each mounting and its engaged bracket on completion of said positioning step to maintain permanently, fixed the angular relationship between each mounting and its respective bracket.

19. The method as set forth in claim 18 wherein said step of pivotally connecting includes the step of disengageably snap fitting the brackets to one another.

20. The method as set forth in claim 18 wherein said step of pivotally interconnecting includes the step of pivotally interconnecting the brackets to one another at two discrete locations disposed along a common pivot axis.

21. The method as set forth in claim 20 wherein said step of pivotally interconnecting includes the steps of disengageably snap fitting the brackets to one another at each of the two discrete locations.

22. The method as set forth in claim 18 wherein each mounting includes one element of a ball and socket joint and wherein another element of the ball and socket joint is disposed at the other end of each bracket and wherein said step of interconnecting comprises the steps of interconnecting one and the other elements to form a ball and socket joint between each mounting and its attached bracket.

23. The method as set forth in claim 19 wherein the element included in each mounting is a socket and wherein the element disposed at the other end of each bracket is a ball and wherein said step of interconnecting comprises the step of inserting each ball into one of the sockets.

24. The method as set forth in claim 23 wherein said step of interconnecting includes the step of retaining each ball in its respective socket to prevent inadvertent disengagement therebetween prior to exercise of said step of fixing.

25. The method as set forth in claim 24 wherein said step of pivotally interconnecting includes the step of pivotally interconnecting the brackets to one another at two discrete locations disposed along a common pivot axis.

26. The method as set forth in claim 25 wherein said step of pivotally interconnecting includes the steps of disengageably snap fitting the brackets to one another at each of the two discrete locations.

27. The method as set forth in claim 18 including the step of retaining each mounting interconnected with its connected bracket during said step of positioning and prior to exercise of said step of fixing, the structure for carrying out said step of retaining being distinct from the structure for carrying out said step of fixing.

28. A method for redintegrating the casts of a dental model throughout a full range of occlusal and masticatory registration to develop a dental prosthetic device mounted on the casts, said method comprising the steps of:
  (a) attaching a mounting to each cast;
  (b) pivotally connecting along a pivot axis one end of a first bracket with one end of a second bracket;
  (c) interconnecting each mounting with the other end of one of the brackets through a ball and socket joint;
  (d) positioning the casts relative to one another at one end of the range of occlusal and masticatory registration to be redintegrated by adjusting the angular relationship between each mounting and its engaged bracket and adjusting the angular relationship about the pivot axis between the pivotally connected ends of the brackets;
  (e) immobilizing the ball and socket joint between connected ones of the mountings and brackets to maintain permanently the fixed angular relationship established between connected ones of the mountings and brackets on completion of said step of positioning;
  (f) flexing the brackets to translate and to rotate the casts relative to one another to determine adjustments necessary to the model teeth or of prosthetic devices or restorations formed thereon;
  (g) alternatively pivoting the casts about the pivot axis of the brackets through an angle of 180° or disengaging the brackets one from the other to permit unrestricted access to the casts for making the adjustments determined in said flexing step;
  (h) alternatively repivoting the casts into registration with one another or reengaging the brackets with one another depending upon whether said pivoting or disengaging step, respectively, was undertaken; and
  (i) repeating said steps of flexing, pivoting and repivoting or disengaging and reengaging until the model teeth, prosthetic device or restoration is developed.

29. The method as set forth in claim 28 wherein the brackets are connected to one another by pivoting snap fits and said steps of disengaging and reengaging comprise the steps of unsnapping and snapping, respectively, the snap fits.

30. The method as set forth in claim 28 including the step of retaining each mounting interconnected with its connected bracket during said step of positioning and prior to exercise of said step of fixing, the structure for carrying out said step of retaining being distinct from the structure for carrying out said step of fixing.

* * * * *